(12) United States Patent
Wood

(10) Patent No.: US 11,883,234 B2
(45) Date of Patent: Jan. 30, 2024

(54) PROBE CABLE SUPPORT

(71) Applicant: B-K Medical Aps, Herlev (DK)

(72) Inventor: Paul G. Wood, Vancouver (CA)

(73) Assignee: BK Medical Aps, Herlev (DK)

( * ) Notice: Subject to any disclaimer, the term of this patent is extended or adjusted under 35 U.S.C. 154(b) by 0 days.

(21) Appl. No.: 17/456,685

(22) Filed: Nov. 29, 2021

(65) Prior Publication Data

US 2022/0079558 A1  Mar. 17, 2022

Related U.S. Application Data

(62) Division of application No. 16/347,023, filed as application No. PCT/IB2016/056626 on Nov. 3, 2016, now Pat. No. 11,202,616.

(51) Int. Cl.
| | | |
|---|---|---|
| *A61B 8/00* | (2006.01) | |
| *H02G 3/04* | (2006.01) | |
| *H02G 3/30* | (2006.01) | |
| *H02G 11/00* | (2006.01) | |

(52) U.S. Cl.
CPC .............. *A61B 8/44* (2013.01); *A61B 8/00* (2013.01); *A61B 8/4405* (2013.01); *H02G 3/0456* (2013.01); *H02G 3/30* (2013.01); *H02G 11/00* (2013.01)

(58) Field of Classification Search
CPC .......... A61B 8/44; A61B 8/00; A61B 8/4405; H02G 3/0456; H02G 3/30; H02G 11/00
USPC ....................... 248/49, 68.1, 74.2, 74.3, 74.5
See application file for complete search history.

(56) References Cited

U.S. PATENT DOCUMENTS

| 4,861,081 A | * | 8/1989 | Satoh | ...................... E05B 79/12 |
| | | | | 292/336.3 |
| 4,991,801 A | * | 2/1991 | Trumbull | ................ F16L 3/221 |
| | | | | 248/62 |
| 6,336,578 B1 | | 1/2002 | Maynard | |
| 6,526,635 B2 | | 5/2003 | Nasu et al. | |
| | | (Continued) | | |

FOREIGN PATENT DOCUMENTS

| WO | 9714904 | 4/1997 |
| WO | 201407593 A1 | 12/2014 |

OTHER PUBLICATIONS

International Search Report for PCT/IB2016/056626 published as WO 2018/083519 dated May 11, 2018.

(Continued)

*Primary Examiner* — Muhammad Ijaz
(74) *Attorney, Agent, or Firm* — Anthony M. Del Zoppo, III; Daugherty & Del Zoppo, Co. LPA

(57) ABSTRACT

A probe cable support (146) includes a leg (202) with a top side (208) and a bottom side (210). The leg further includes a plurality of supports ($216_1$, $216_2$, . . . , $216_N$) protruding from the bottom side and intermittently arranged with non-zero gaps there between. The leg further includes an arm (226) protruding from the top side. A system (101) includes an ultrasound imaging system (100) configured with at least one probe (102) and a console (104), a cable (116) configured to electrically connect the probe and the console, a cart (106) configured to support the ultrasound imaging system, and a probe cable support (146) configured to support the cable.

20 Claims, 6 Drawing Sheets

(56) References Cited

U.S. PATENT DOCUMENTS

| | | | | |
|---|---|---|---|---|
| 6,629,927 B1* | 10/2003 | Mesaros | ................ | A61B 50/13 |
| | | | | 600/437 |
| 6,631,876 B1* | 10/2003 | Phillips | .................... | F16B 2/22 |
| | | | | 248/74.2 |
| 6,643,900 B2* | 11/2003 | Jahrling | ................. | F16B 12/38 |
| | | | | 24/339 |
| 6,802,480 B1 | 10/2004 | Martello | | |
| 9,334,887 B2 | 5/2016 | Leo, II et al. | | |
| 10,240,820 B2* | 3/2019 | Ash | ....................... | F24S 25/636 |
| 2008/0009728 A1* | 1/2008 | Malchow | ............. | A61B 8/0841 |
| | | | | 600/562 |
| 2008/0132789 A1* | 6/2008 | Malchow | ............. | A61B 8/0841 |
| | | | | 600/443 |
| 2010/0102175 A1* | 4/2010 | Dockery | ................. | H02G 3/32 |
| | | | | 248/62 |
| 2011/0201927 A1* | 8/2011 | Hayakawa | .............. | A61B 8/46 |
| | | | | 600/437 |
| 2016/0355374 A1* | 12/2016 | Sinnett | ................. | B65H 75/366 |
| 2018/0132822 A1* | 5/2018 | Stankard | ............. | A61B 8/4433 |
| 2019/0356118 A1* | 11/2019 | Capulli | .................. | H02G 3/045 |

OTHER PUBLICATIONS

U.S. Appl. No. 16/347,023, filed May 2, 2019, Confirmation No. 8259.

\* cited by examiner

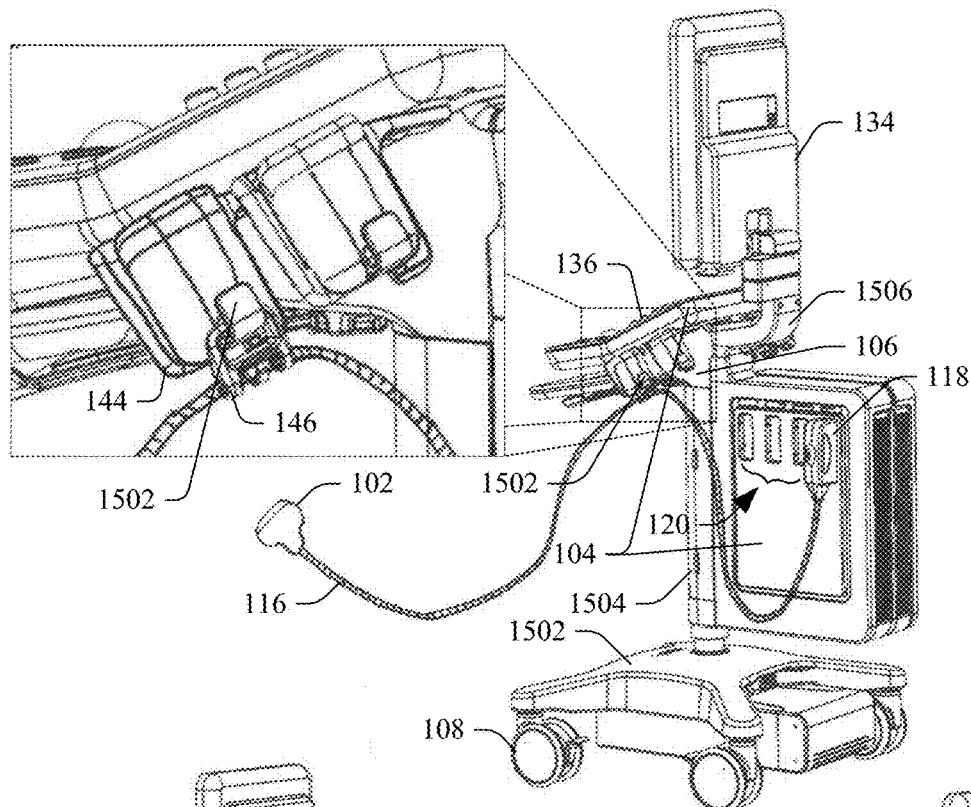
FIGURE 15
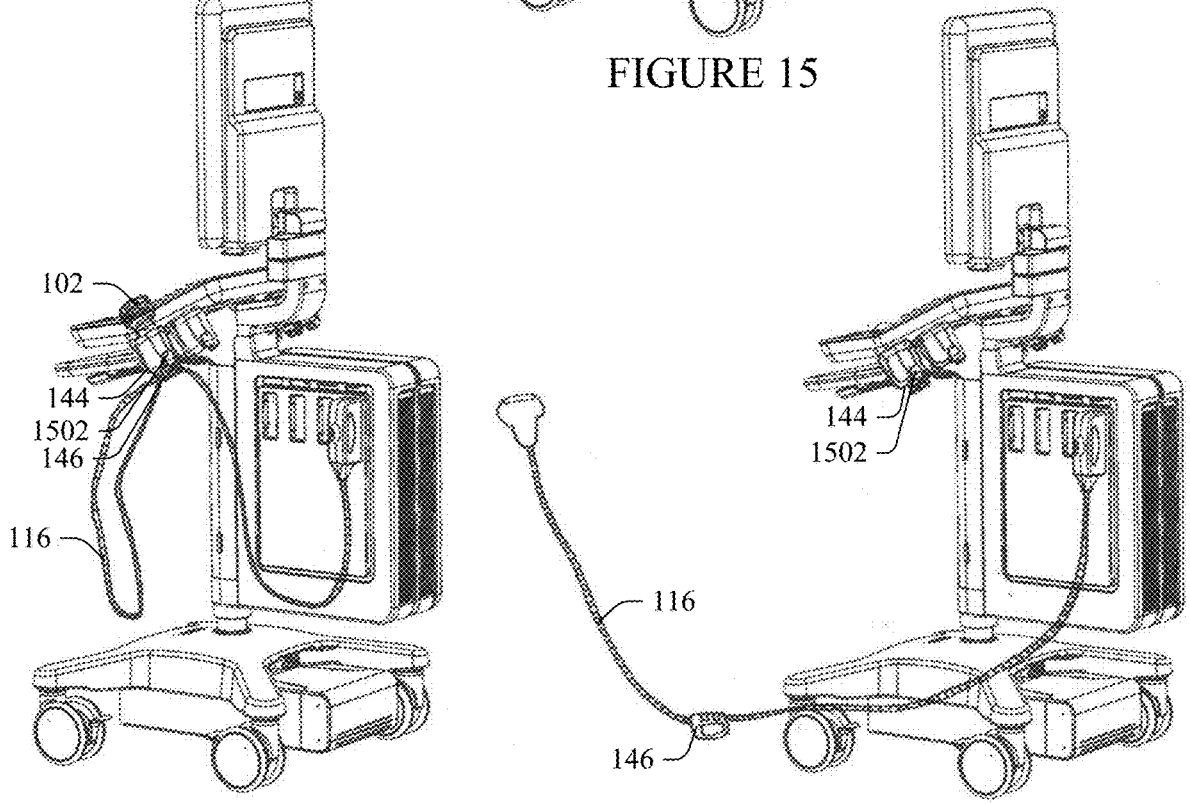
FIGURE 16
FIGURE 17

PROBE CABLE SUPPORT

TECHNICAL FIELD

The following generally relates to a probe cable support and is described with particular application to an ultrasound imaging probe cable support, but is also amenable to other types of cables.

BACKGROUND

Ultrasound imaging provides information about the interior of a subject. An ultrasound imaging system has included a console and a probe with a cable that connects the probe to the console. The console has been placed on a cart with wheels, which can be moved around. With such a system, a length of the cable may be such that it hangs down and touches the ground. As a consequence, the cable may be damaged. For example, when the cart is moved the cable may get pinched under a wheel(s). Existing probe cable management solutions require the user to judge how to best place cables onto the system. The user must exercise care every time a cable is placed onto the system to prevent damage. Cables, which are initially placed carefully, are often displaced as the system is moved and eventually touch the floor putting them at risk for damage. As such, there is an unresolved need for another probe cable management solution.

SUMMARY

Aspects of the application address the above matters, and others.

In one aspect, a probe cable support includes a leg with a top side and a bottom side. The leg further includes a plurality of supports protruding from the bottom side and intermittently arranged with non-zero gaps there between. The leg further includes an arm protruding from the top side.

In another aspect, a system includes an ultrasound imaging system configured with at least one probe and a console, a cable configured to electrically connect the probe and the console, a cart configured to support the ultrasound imaging system, and a probe cable support configured to support the cable.

In another aspect, a method includes receiving a cable in a channel of a probe cable support, which secures the cable in the channel of the probe cable support, wherein the cable is a cable from an ultrasound imaging system to a console of the ultrasound imaging system, and receiving a loop of the probe cable support on a hook of a cart supporting the ultrasound imaging system.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which:

FIG. 15 schematically illustrates an example of the ultrasound imaging in connection with the probe removed from the probe support on the cart and the probe cable support hooked on the probe support;

FIG. 16 schematically illustrates an example of the ultrasound imaging in connection with the probe installed in the probe support and the probe cable support hooked on the probe support;

FIG. 17 schematically illustrates an example of the ultrasound imaging in connection with the probe removed from the probe support on the cart and the probe cable support unhooked from the probe support;

DETAILED DESCRIPTION

The following generally discloses a cable support that secures a cable to an apparatus. The cable support can mitigate cable damage, e.g., in connection with the cable contacting and/or lying on the floor. For sake of brevity and explanatory purposes, the following is described in connection with an ultrasound imaging system. However, it is to be understood that the cable support can be used to support other cables in connection with other systems.

Figure 1:
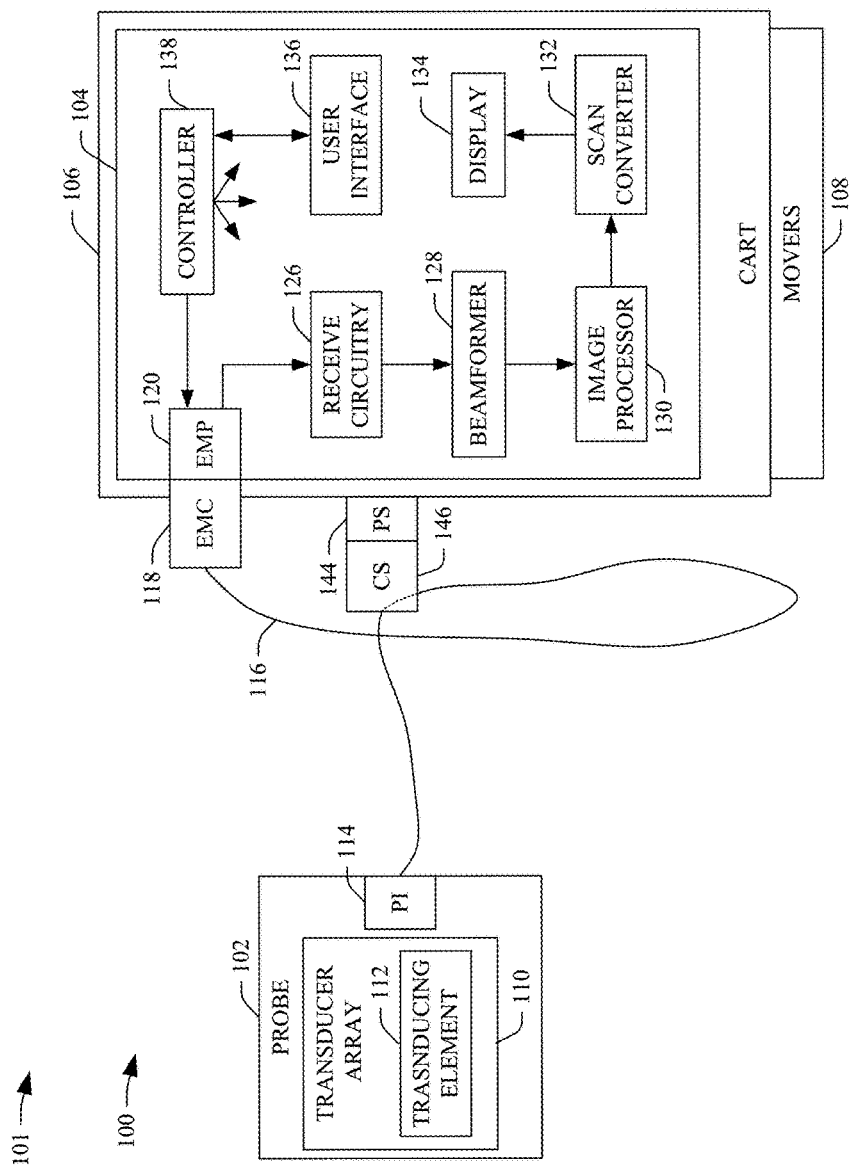
FIG. 1 schematically illustrates an example ultrasound imaging system in connection with a probe cable support.

FIG. 1 schematically illustrates a system 101 including an example ultrasound imaging system 100. The ultrasound imaging system 100 includes a probe 102 and a console 104. The ultrasound imaging system 100 is supported by a cart 106 with movers 108 such as wheels, castors, rollers, or the like. In a variation, the ultrasound imaging system 100 is alternatively placed on another mobile device or on a stationary apparatus such as a table, counter top, cart without wheels, or the like.

The probe 102 includes a transducer array 110 with one or more transducing elements 112. The transducer array 110 can be a one one-dimensional (1-D) transducer array or a two-dimensional (2-D) transducer array. The transducing elements 112 are configured to emit an ultrasound beam or pressure wave in response to being excited by an electrical pulse. The transducing elements 112 are further configured to receive an echo or pressure wave, which is generate in response to the emitted ultrasound beam or wave interacting with structure, and produce an electrical signal indicative of the received echo or pressure wave.

The probe 102 further includes a probe interface (PI) 114 and a cable 116. A first end of the cable 116 is connected to the probe interface 114. A second opposing end of the cable 116 include an electro-mechanical connector (EMC) 118 (e.g., with pins, etc.). The console 104 includes an electro-mechanical port (EMP) 120 (e.g., with sockets, etc.). The electro-mechanical port 120 is complementary to the electro-mechanical connector 118 and is configured to engage the electro-mechanical port 120 and establish electrical communication there between. The probe 102 and the console 104 electrically communicate via the electro-mechanical connector 118/electro-mechanical port 120 connection.

Receive circuitry 126 receives the electrical signal produced by the transducing elements 112. In one instance, the receive circuitry 126 pre-processes or conditions the electrical signal, e.g., amplifies the signal. A beamformer 128 processes the electrical signal or the pre-processed/conditioned electrical signal. This includes applying time delays, weighting the channels, and summing the weighted signals, and/or otherwise beamforming received echoes, producing data for generating images in A-mode, B-mode, Doppler, and/or other ultrasound imaging modes.

An image processor 130 processes the beamformed data. For B-mode, this may include generating a sequence of focused, coherent echo samples along focused scanlines of a scanplane. The image processor 130 may also be configured to process the scanlines to lower speckle and/or improve specular reflector delineation via spatial compounding, apply filtering such as FIR and/or IIR, etc. A scan converter 132 converts the output of the image processor 118 and generates data for display, for example, by converting the data to the coordinate system of the display.

A display 134 is configured to display ultrasound information such as images, etc. In one instance, the display 134 is part of the console 104. For example, the console 104 can be configured similar to a laptop computer with a built in display. In another instance, the display 134 is a separate display monitor. In this instance, the console 104 and the display 134 communicate via a hard wired connection (e.g., a cable) and/or wireless communication. Also in this instance, the display 134 can be placed near the console 104 or remote therefrom such as in a different room.

A user interface 136 includes one or more input devices (e.g., a button, a knob, a slider, a touch pad, etc.) and/or one or more output devices (e.g., a display screen, lights, a speaker, etc.). The user interface 136 can be used to select an imaging mode, select an imaging protocol, commence imaging, etc.

The console 104 further includes a controller 138, which controls one or more of the electrical connections of the console 104. The controller 138 also controls whether the probe 102 is in transmit or receive mode. In transmit mode, the controller 138 transmits a predetermined set of pulses to the probe 102, and the set of pulses excite a predetermined set of the transducing elements 112 to emit the ultrasound beam. For receive mode, the controller 138 transmits a control signal that causes the transducing elements 112 to receive an echo or pressure wave.

It is to be understood that the components 126, 128, 130, 132, 134, 136 and 138 are provided for explanatory purposes and are not limiting. In other embodiments, the console 104 may include more, less and/or different components.

The console 104 is mounted to or supported on the cart 106, which is mobile via the movers 108 such as wheels, casters, rollers, or the like. In another instance, the console 104 can be configured to be alternatively removably installed on the cart 106 and/or other cart(s), a wall mount, or a tabletop support. An example of this is described in US publication 2011/0118562 A1, entitled "Portable ultrasound scanner," and filed on Nov. 17, 2009, which is incorporated herein in its entirety by reference.

The cart 106 includes a probe support (PS) 144. In a variation, the console 104 includes the probe support 144. The probe support 144 is configured to physically support or hold the probe 102, e.g., when the probe 102 is not in use. In one instance, the probe support 144 is fixedly mounted to the cart 106. In another instance, the probe support 144 is an integral part of the cart 106, e.g., part of a handle and/or other portion of the cart 106. In yet another instance, the probe support 144 is removably installed on the cart 106.

A probe cable support (CS) 146 is supported by the probe support 144. As described in greater detail below, the probe cable support 146 is configured to support the cable 116 via the cart 106. In one instance, the probe cable support 146 ensures that the cable 116 is placed correctly onto the cart 106 without requiring undue care or thought on the part of the user, while preventing the cable 116 from touching the floor. This can mitigate damage to the cable 116, e.g., from the movers 108 rolling over the cable 116. Additionally or alternatively, the probe cable support 146 ensures the cable 116 remains in that position after it is installed on the cart 106. The probe cable support 146 can be quickly and easily installed and/or removed from the probe support 144, while the probe cable support 146 grips the cable 116 with enough force to maintain the position of the probe cable support 146 along a length of the cable 116.

Figure 2:
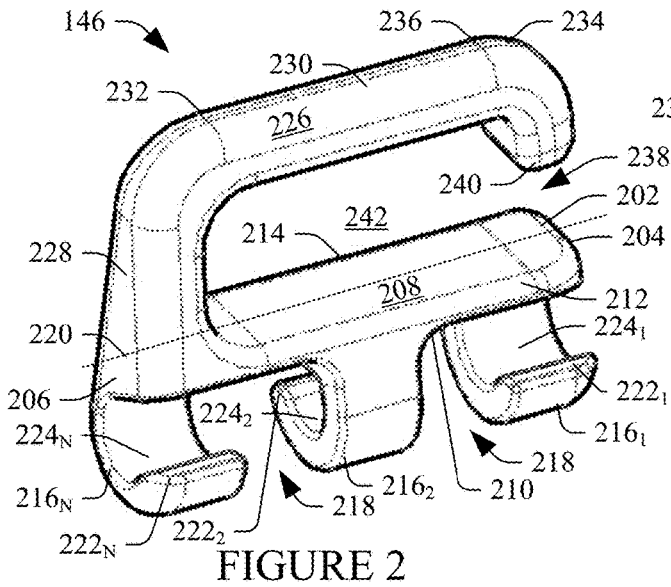
FIG. 2 schematically illustrates a perspective view of the probe cable support.
Figure 4:
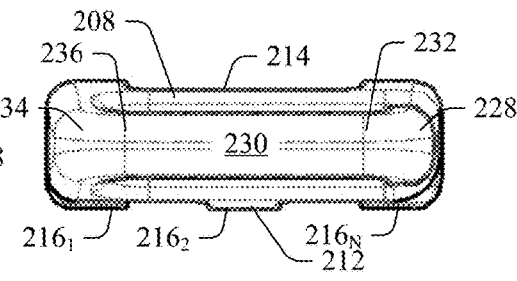
FIG. 4 schematically illustrates a top down view of the probe cable support.
Figure 3:
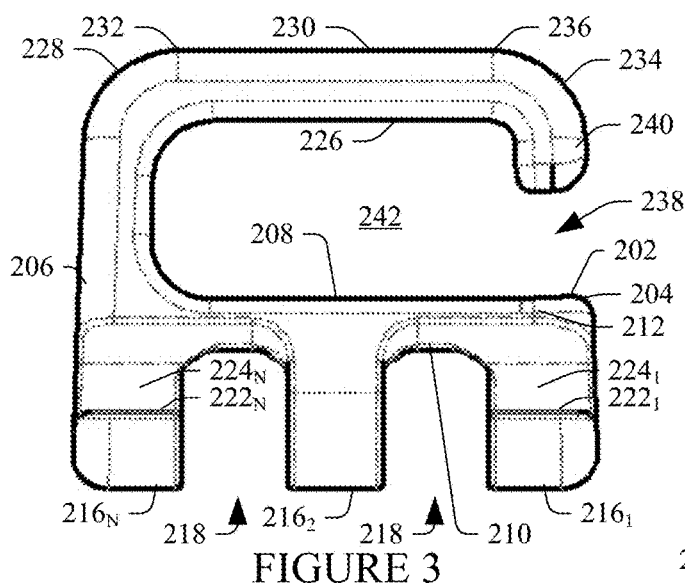
FIG. 3 schematically illustrates a front view of the probe cable support.
Figure 5:
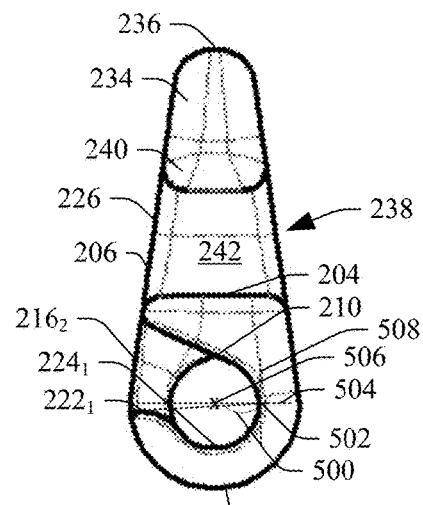
FIG. 5 schematically illustrates a side view of the probe cable support.
Figure 6:
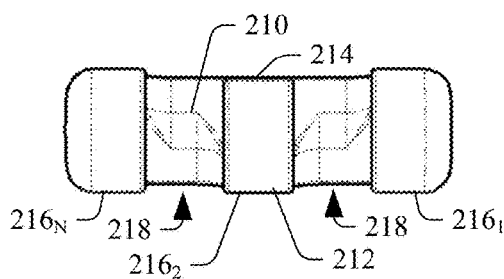
FIG. 6 schematically illustrates a bottom up view of the probe cable support.

FIGS. 2, 3, 4, 5 and 6 illustrate an example of the probe cable support 146. FIG. 2 shows a perspective view, FIG. 3 shows a front view, FIG. 4 shows a top down view, FIG. 5 shows a side view, and FIG. 6 shows a bottom up view.

In this example, the probe cable support 146 includes a first leg 202. The first leg 202 includes a first end 204, an opposing or second end 206 which opposes the first end 204, a top side 208 between the first and second end 204 and 206, a bottom side 210 between the first and second end 204 and 206 and opposing the top side 208, a front side 212 between the first and second end 204 and 206 and the top and bottom sides 208 and 210, and a back side 214 between the first and second end 204 and 206 and the top and bottom sides 208 and 210 and opposing the front side 212.

A plurality of hooks or supports $216_1$, $216_2$, ..., $216_N$ (where N is a positive integer) protrude from the bottom side 210. In this example, N=3. In another example, N=1. In another example, N=2. In yet another example, N>3. Each of the supports $216_1$, $216_2$, ..., $216_N$ protrudes down and is "J" shaped, with the support $216_1$ at the first end 204, the support $216_N$ at the second end 206, and the support $216_2$ there between. The supports $216_1$, $216_2$, ..., $216_N$ are arranged intermittently in that neighboring pairs are separated by non-zero gaps 218 along a direction of a long axis 220. In a variation, at least one of the gaps 218 is omitted.

The supports $216_1$ and $216_N$ protrude from the bottom side 210 at a region near the back side 214 with hook ends $222_1$ and $222_N$ of the "J" at the front side 212. The support $216_2$ protrudes from the bottom side 210 at a region near the front side 212 with hook end $222_2$ of the "J" at the back side 214. In a variation, one or more of the supports $216_1$, $216_2$, ..., $216_N$ can be reversed such that the "J" faces the other direction. The intermittent supports $216_1$, $216_2$, ..., $216_N$ allow the cable 116 to be easily inserted and removed when the supports are position in opposing directions. The opposing design of the supports $216_1, 216_2, \ldots, 216_N$ allows the cable support 146 to attach securely to the cable 116 while also being easy to remove and re-attach, allowing the probe cable support 146 to grip and hold the cable 116 tightly in place. In another variation, the supports $216_1$ and $216_2$ face the same direction and the support $216_N$ faces the opposing direction. In another variation, the supports $216_2$ and $216_N$ face the same direction and the support $216_1$ faces the opposing direction. In another variation, all of the supports $216_1, 216_2, \ldots, 216_N$ face a same direction.

As described in greater detail below, the probe cable support 146 supports the cable 116 (FIG. 1) in respective channels $224_1, 224_2, \ldots, 224_N$ of the supports $216_1, 216_2, \ldots, 216_N$, between the channels $224_1, 224_2, \ldots, 224_N$ and the bottom side 210 of the first leg 202. A radius of curvature of the channels $224_1, 224_2, \ldots, 224_N$ is configured to be smaller than a radius of the cable 116 such that the cable 116 is engaged when installed in the supports $216_1, 216_2, \ldots, 216_N$. As shown in FIG. 5, the hook of the "J" extends an angle 500 (e.g., 135°, 180°, or other angle, e.g., between 45° and 225°) from an intersection 502 a horizontal axis 504 through a center 506 of the channels $224_1, 224_2, \ldots, 224_N$ and a vertical axis 508 perpendicular to the horizontal axis 504. The channels $224_1, 224_2, \ldots, 224_N$ can be circular (as shown), oval, and/or otherwise shaped.

Generally, a single angle in the range of 45° to 225° is well-suited for configurations in which the at least two of the supports $216_1, 216_2, \ldots, 216_N$ face opposite directions, such as shown in FIGS. 2-6. For example, in one embodiment the angle in FIGS. 2-6 is 45°. In another embodiment, this angle is 60°. In another embodiment, this angle is 90°. In another embodiment, this angle is 135°. In another embodiment, this angle is 225°. The enumerated angles are not limiting, and other single angles are also contemplated herein. In addition, the range of 45° to 225° is not limiting.

An arm 226 includes a first member 228 that protrudes up from the top side 208 at the second end 206 in a direction opposite of the support $216_N$, a straight second member 230 that extends from an end 232 of the first member 228 in a direction transverse to the first member 228 and along the axis 220, and a third member 234 that extends from an end 236 of the straight second member 230 in a direction transverse to the second member 230 and towards the top side 208, with a gap 238 between an end 240 of the third member 234 and the top side 208. The arm 226 forms a "hook" or an open oval or ring with a material free region 242 between the arm 226 and the top side 208.

The cable support 146 is small and light enough that it doesn't hinder the use of the probe 102 after it is attached. The teardrop shape shown in FIG. 5 renders the probe cable support 146 easy to clean and slim fitting on the cable 116. The top 230 of the probe cable support 146, in the illustrated example, is filleted (round) to rotate freely when placed on the cart 106. The open loop design renders the probe cable support 146 versatile, allowing a variety of attachment points near the cart 106, such as the patient bedside or clothing worn by the sonographer. The open loop configuration also allows the cable 116 to be supported close to the user during a scan so that the user does not need to support the weight of the cable 116, in addition to the weight of the probe, during a procedure. The cable support 146 offers a simple solution for preventing damage to probe cable 116 giving close consideration to how ultrasound systems are used in the field.

FIGS. 7, 8, 9, 10, 11, 12, 13 and 14 illustrate a non-limiting set of variations of the probe cable support 146.

Figure 7:
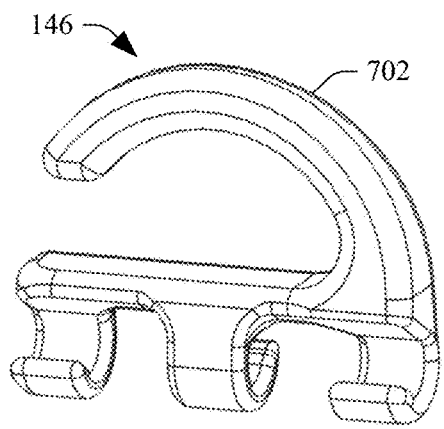
FIG. 7 schematically illustrates a variation of the probe cable support.
Figure 8:
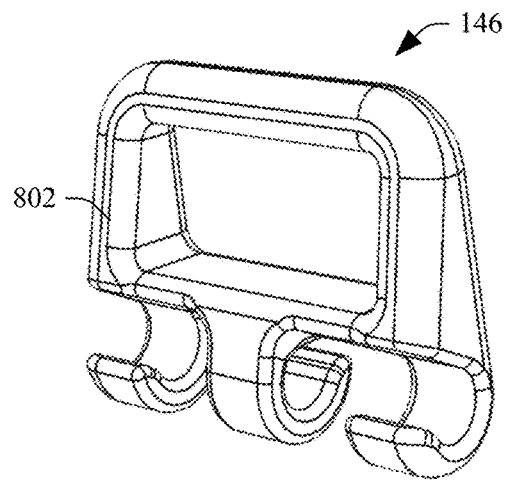
FIG. 8 schematically illustrates another variation of the probe cable support.

FIG. 7 is substantially similar to the embodiment of FIG. 2-6 except the arm 226 is a single curved (e.g., convex or "u" shaped) member or arch 702 instead of the series of transverse members (228, 230, 234). FIG. 8 is substantially similar to the embodiment of FIG. 2-6 except the end 240 of the third member 234 extends to and is integrated with the first end 204 of the top side 208, forming a closed oval or ring 802.

Figure 9:
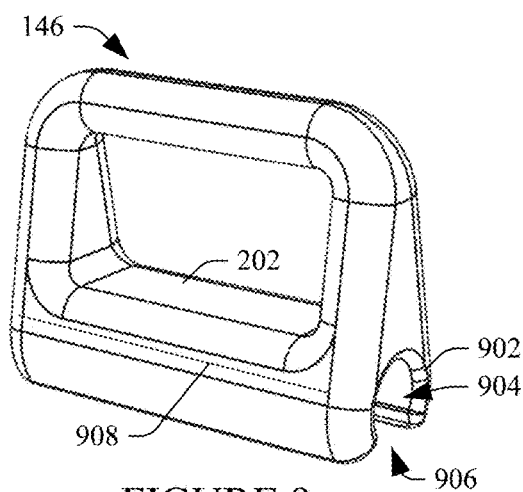
FIG. 9 schematically illustrates another variation of the probe cable support.
Figure 10:
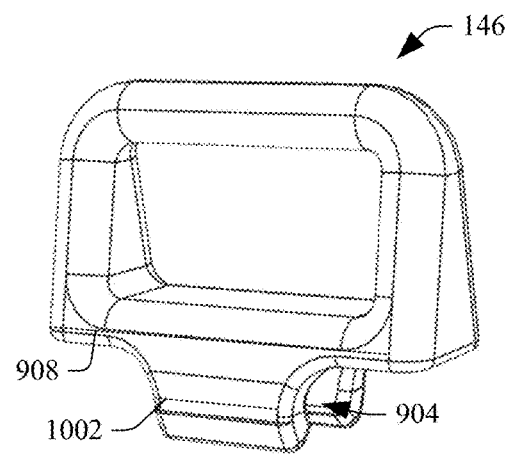
FIG. 10 schematically illustrates another variation of the probe cable support.

In FIG. 9, like FIG. 8, the end 240 of the third member 234 extends to and is integrated with the first end 204 of the top side 208, forming a closed configuration. In addition, a single support 902 with a channel 904 (e.g., "C" shaped) extends from the bottom side 210 with an opening 906 of the channel 904 facing down, instead of the supports $216_1, 216_2, \ldots, 216_N$. In FIG. 9, the channel 904 extends a length 908 of the first leg 202. FIG. 10 is substantially similar to FIG. 9 except the channel 904 extends a shorter distance, e.g., a first length 1002, which is less than the length 908. In these embodiments, the angle of each branch of the "C" is a single angle from 45° to 135°. The illustrated angle is on an order of 135°. The range of 45° to 135 is not limiting, as smaller and/or larger angles are contemplated herein.

In another variation, the channel 904 extends a greater distance than the length 908. Furthermore, the channel 904 can be "C" shaped, "U" shaped, and/or otherwise shaped to include an entrance for the cable 116 to be installed therein. FIGS. 9 and 10 generally represent bottom mount installation configurations. The radius of the channel 904 is similar to that of the channels $224_1, 224_2, \ldots, 224_N$ at least in that the channel 904 is configured to be smaller than a radius of the cable 116 such that the cable 116 is physically engaged by the channel 904 when the cable 116 is installed therein.

Figure 11:
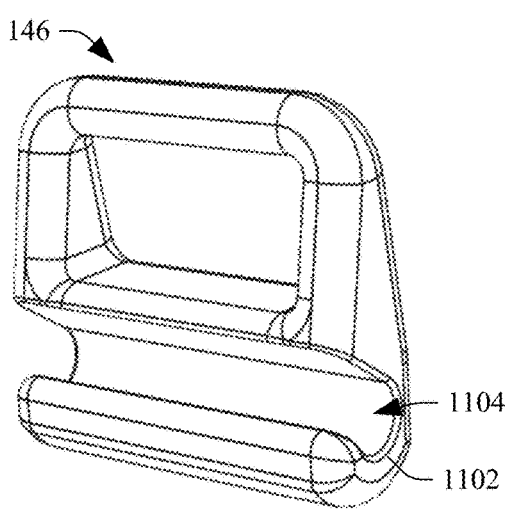
FIG. 11 schematically illustrates another variation of the probe cable support.

In FIG. 11, like FIG. 8, the end 240 of the third member 234 extends to and is integrated with the first end 204 of the top side 208, forming a closed configuration. In addition, a single "J" shaped support 1102 with a channel 1104 extends from the bottom side 210. The radius of the channel 1104 is similar to that of the channels $224_1, 224_2, \ldots, 224_N$ at least in that the channel 1104 is configured to be smaller than a radius of the cable 116 such that the cable 116 is physically engaged by the channel 1104 when the cable 116 is installed therein. FIG. 11 generally represents a single side mount installation configuration. In these embodiments, the angle is a single angle from 90° to less than 225°. The illustrated angle is on an order of 180°. The range of 90° to 225° is not limiting, as smaller and/or larger angles are contemplated herein.

Figure 12:
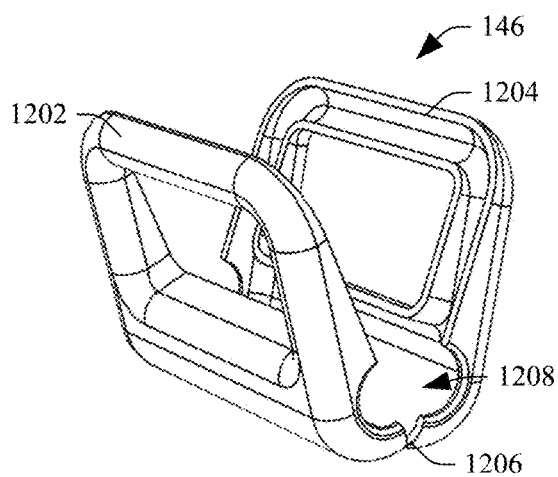
FIG. 12 schematically illustrates another variation of the probe cable support.

In FIG. 12, the probe cable support 146 includes a front half 1202 and a back half 1204, which are pivotally connected at a hinge 1206 such that pivoting one or both of the halves 1202 and 1204 opens and closes the probe cable support 146. The probe cable support 146 further includes a channel 1208. When the one or both of the halves 1202 and 1204 are pivoted away from each other, the channel 1208 opens (as shown), allowing the cable 116 to be installed therein. When the one or both of the halves 1202 and 1204 are pivoted toward each other, the halves of the channel 1208 close around the cable 116, securing the cable 116 therein. The halves 1202 and 1204 can lock together via a mechanism such as a snap or the like.

In FIGS. 2-12, the arm 206 and the supports $216_1, 216_2, \ldots, 216_N$ respectively extend from opposing sides 208 and 210. In this configuration, the probe cable support 146 forms an "I" like shape from a side view, as shown in FIG. 5. In a variation, one of the arms 226 or the supports $216_1$, $216_2, \ldots, 216_N$ extend from one of the front side 212 or the back side 214. In this configuration, the probe cable support 146 forms an "L" like shape from a side view.

Figure 13:
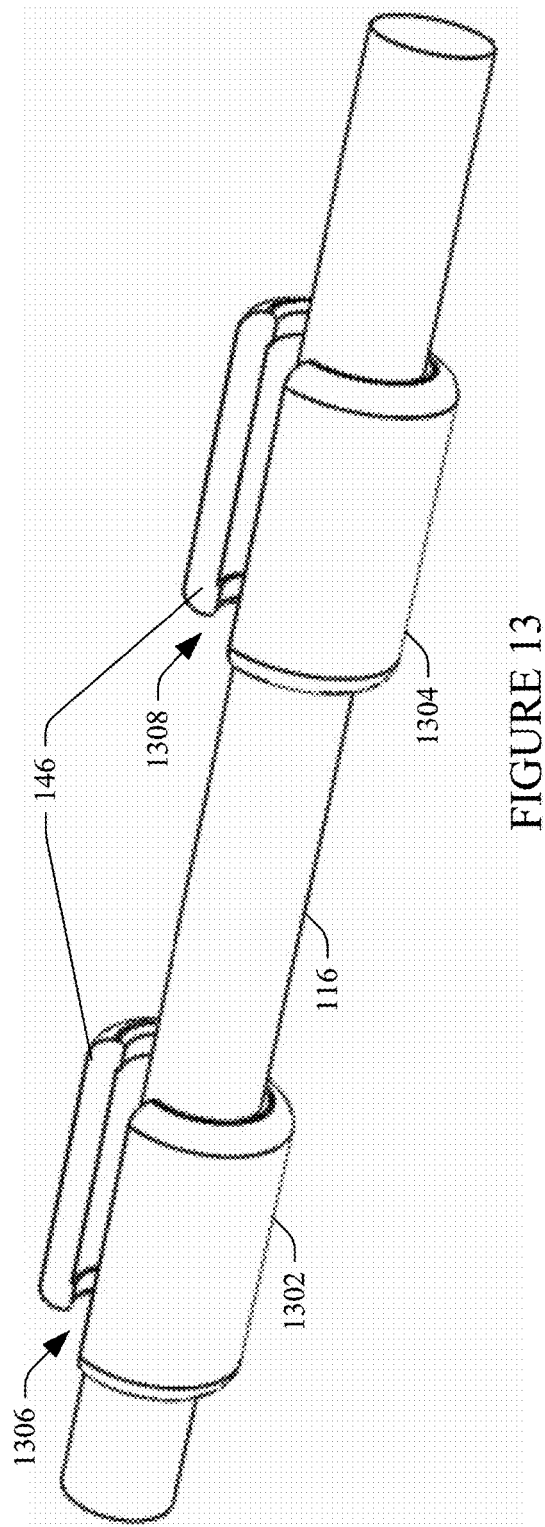
FIG. 13 schematically illustrates another variation of the probe cable support.
Figure 14:
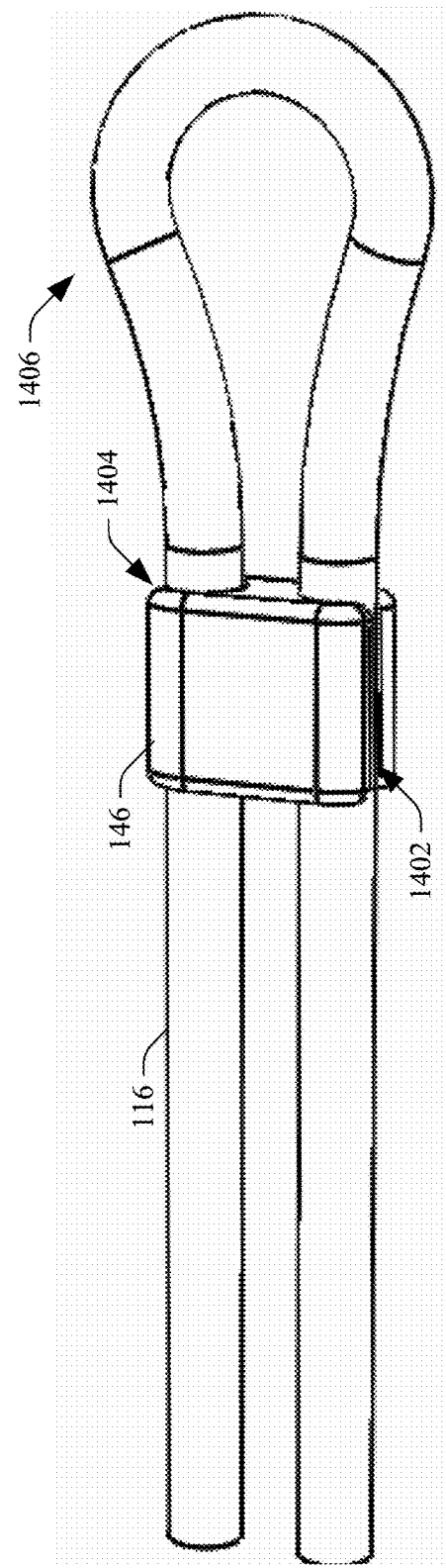
FIG. 14 schematically illustrates another variation of the probe cable support.

FIG. 13 shows a configuration in which the probe cable support 146 includes two separate supports 1302 and 1304, each with a channel 1306 and 1308 configured to receive and engage the cable 116, securing the cable 116 therein. With this variation, the two supports 1302 and 1304 are statically fixed on the cable 116 and separated by a gap, and a portion of the cable 116 in the gap is hooked on the probe support 144 of the cart 106. FIG. 14 shows a configuration in which the probe cable support 146 includes two channels 1402 and 1404, the cable 116 is feed through the two channels 1402 and 1404 forming a loop 1406, which is hooked on the probe support 144 of the cart 106.

FIGS. 15, 16 and 17 illustrate an example of the ultrasound imaging system 100 in connection with the cable support 146 described in connection with FIG. 8. In this example, the cart 106 includes a base 1502 to which the movers 108 (wheels in this example) are affixed. A post 1504 protrudes up from the base 1502 and includes a support configured to support the console 104, which comprises two parts in this example. A bracket 1506 is configured to support the display 134.

FIG. 15 shows the ultrasound imaging system 100 with the probe 102 removed from the probe support 144, the probe cable support 146 engaging the cable 116 and secured on a hook 1502 of the probe support 144, and the cable 116 extended and supported by the probe cable support 146. In a typical use case, the probe cable support 146 would be affixed to the cable 116 once and remain there. The location of the probe cable support 146 is such that enough cable is free to perform ultrasound procedures without the cable 116 touching the floor or otherwise getting pinched by the movers 108. In a variation, the location of the probe cable support 146 on the cable 116 can be changed, before, during and/or after use of the probe 102.

FIG. 16 shows the ultrasound imaging system 100 with the probe 102 installed in the probe support 144 with the cable 116 installed in the cable support 146, which is secured on the hook 1502. This generally represents the case when the probe 102 is not being used for imaging, e.g., when being stored. Similar to FIG. 15, the cable support 146 supports the cable 116 so that the cable 116 does not touch the floor or otherwise can be pinched by the movers 108. Although only a single probe 102 is shown, this example includes at least one more probe support 144, and multiple probe supports 144 can support multiple probes 102 concurrently, wherein probe cable supports 146 are utilized with the cables 116 of each of the probes 102.

Figure 18:
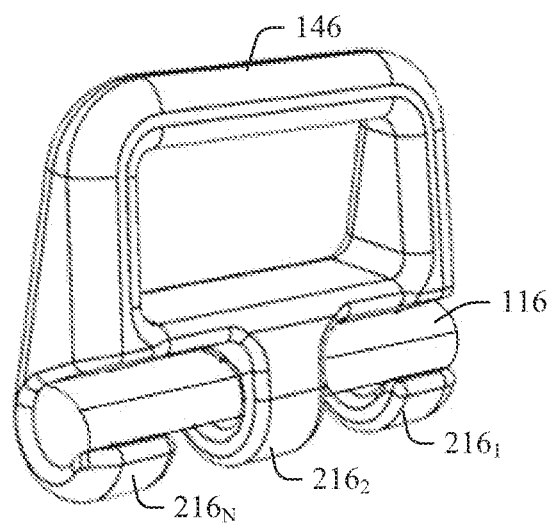
FIG. 18 schematically illustrates an example of the probe cable support with a cable installed therein.

FIG. 17 is similar to FIG. 15 except the probe cable support 146 is removed from the hook 1502. Removing the cable support 146 from the hook 1502 is well-suited for instances in which more cable 116 length is needed to perform an ultrasound imaging procedure. The cable support 146 can later be placed on the hook 1502 for further scanning and/or after scanning is complete. In a variation, the cable 116 includes more than one probe cable support 146 located at different positions along the cable 116. With this variation, the user can switch from one probe cable support 146 to another to lengthen or shorten the amount of cable 116. FIG. 18 shows the cable 116 installed the probe cable support 146.

Figure 19:
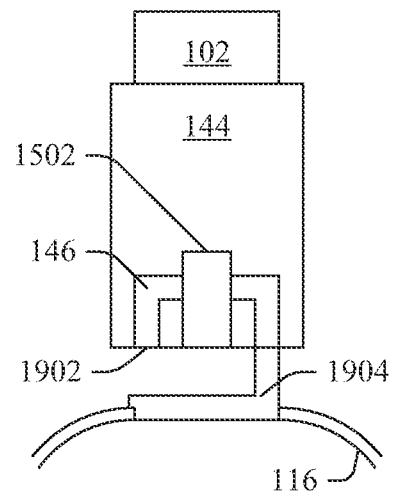
FIG. 19 schematically illustrates an example of another probe cable support with a cable installed therein and the probe cable support installed on the probe support on the cart.

FIG. 19 shows the cable 116 installed in yet another variation of the cable support 146, which is hooked on the hook 1502 of the probe support 144. This variation is a combination of FIGS. 2-6 and 9 with an open ring hook 1902 and a single channel 1904 in which the cable 116 is installed.

The probe cable support 146 includes a single or multiple components that can be quickly and easily attached (or removed) to the cable 116. The probe cable support 146 can be configured for a family of probes. Multiple cable supports 146 can be used where different probes use different diameter cables, although a single cable support will accommodate some variance in cable diameter. In one instance, the cable support 146 is configured to maintain its position along the length of the cable 116 without sliding. Once secured to the cable 116, the hook and cable support 146 can be attached the probe support 144 and/or other component of the system 100. Multiple cable supports 146 can be installed on the cable 116 at different locations, e.g., where a plurality of locations is identified for different procedures and/or different users.

The probe cable support 146 can attach directly to the cable 116 and maintains a fixed position along the length of the cable 116 using opposing, intermittent spaces hooks. It can be attached or removed easily without the use of a tool or any moving parts. It is small and light enough to go undetected while using the ultrasound probe. Placing the cable support 146 at a fixed distance along the length of the probe cable ensures that the user places the cable 116 onto the system 100 correctly every time and that the cable 116 remains in the correct position to prevent any unwanted cable damage. The open hook configuration (e.g., FIGS. 2-7) allows the user to secure the cable 116 during a scan to attachment points not necessarily located on the ultrasound cart.

In one instance, the cable support 146 is injection molded, which can produce the support at a sufficiently low cost to serve as a disposable. The cable support 146 can also be molded in a sterilizable material for part sterilization and re-use in a hospital setting. Other molding methods, such as reaction injection molding, compression molding and rotational molding are contemplated herein. In low production quantities, the part could be produced using 3D printing methods such as fused deposition modeling or stereolithography. It would also be possible to machine this support. Regardless of production method, the support should be constructed of a material that is sufficiently strong to resist breaking under load, such as when it is stepped on, but also light enough to add no noticeable weight to the probe cable. Many plastics would serve as an example of such a material.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A system, comprising:
   an ultrasound imaging system configured with at least one probe and a console;
   a cable configured to electrically connect the probe and the console;
   a cart configured to support the ultrasound imaging system, wherein the cart includes a cable support hook; and
   a probe cable support configured to support the cable, wherein the probe cable support includes:
   a leg, including:
   a long axis, including:
   a first end; and
   a second end opposing the first end, a top side between the first and second ends and facing a first direction; and a bottom side between the first and second ends, below the top side, and facing a second direction, which opposes the first direction;

an arm protruding up from the first end of the top side and extending along the long axis and over the top side of the leg to the second end, forming a ring with a material free region between the arm and the top side of the leg, wherein the arm is configured to engage the cable support hook of the cart; and a support protruding from the bottom side below the arm and configured to support the cable.

2. The system of claim 1, wherein the support includes at least one hook.

3. The system of claim 2, wherein the at least one hook includes three hooks.

4. The system of claim 3, wherein at least two of the three hooks face different directions.

5. The system of claim 4, wherein at least one of the three hooks includes a channel.

6. The system of claim 5, wherein the material free region is inside of the ring, and the ring is a closed ring.

7. The system of claim 6, wherein the arm is rectangular shaped.

8. The system of claim 5, wherein the material free region is inside of the ring and the ring is an open ring.

9. The system of claim 8, further including a gap between the arm and the second end.

10. The system of claim 8, wherein the arm is arch shaped.

11. The system of claim 2, wherein the at least one hook includes a single channel with an opening that faces down and away from the support.

12. The system of claim 11, wherein the single channel extends an entire length of the leg.

13. The system of claim 11, wherein the leg extends a first length, the single channel extends a second length, and the first length is greater than the second length.

14. The system of claim 11, wherein the leg extends a first length, the single channel extends a second length, and the first length is less than the second length.

15. The system of claim 11, wherein the single channel is "C" shaped.

16. The system of claim 11, wherein the single channel is "U" shaped.

17. The system of claim 1, wherein the at least one hook includes a single channel with an opening facing out of a side of the support.

18. The system of claim 17, further comprising: a front half and a back half.

19. The system of claim 18, wherein the front half and the back half are pivotally connected at a hinge.

20. The system of claim 19, wherein the at least one hook includes a single channel disposed above the hinge.

* * * * *